(12) United States Patent
Guracar

(10) Patent No.: US 8,668,648 B2
(45) Date of Patent: Mar. 11, 2014

(54) CONTRAST AGENT DESTRUCTION EFFECTIVENESS DETERMINATION FOR MEDICAL DIAGNOSTIC ULTRASOUND IMAGING

(75) Inventor: Ismayil M. Guracar, Redwood City, CA (US)

(73) Assignee: Siemens Medical Solutions USA, Inc., Malvern, PA (US)

( * ) Notice: Subject to any disclaimer, the term of this patent is extended or adjusted under 35 U.S.C. 154(b) by 1287 days.

(21) Appl. No.: 12/011,099

(22) Filed: Jan. 23, 2008

(65) Prior Publication Data

US 2009/0187103 A1 Jul. 23, 2009

(51) Int. Cl.
*A61B 8/14* (2006.01)

(52) U.S. Cl.
USPC ............................ 600/458; 600/438; 600/439

(58) Field of Classification Search
USPC .......................... 600/438, 439, 458
See application file for complete search history.

(56) References Cited

U.S. PATENT DOCUMENTS

| | | | | |
|---|---|---|---|---|
| 5,657,760 | A * | 8/1997 | Ying et al. | 600/439 |
| 5,833,613 | A * | 11/1998 | Averkiou et al. | 600/440 |
| 5,860,931 | A | 1/1999 | Chandler | |
| 5,971,928 | A * | 10/1999 | Dodd et al. | 600/458 |
| 6,077,225 | A * | 6/2000 | Brock-Fisher | 600/439 |
| 6,080,107 | A | 6/2000 | Poland | |
| 6,086,540 | A * | 7/2000 | Bonneville et al. | 600/458 |
| 6,340,348 | B1 | 1/2002 | Krishnan et al. | |
| 6,464,643 | B1 * | 10/2002 | Brock-Fisher | 600/458 |
| 6,494,841 | B1 | 12/2002 | Thomas et al. | |
| 6,602,195 | B1 | 8/2003 | Krishnan et al. | |
| 6,632,177 | B1 | 10/2003 | Phillips et al. | |
| 6,638,228 | B1 | 10/2003 | Brock-Fisher et al. | |
| 6,682,482 | B1 | 1/2004 | Krishnan | |
| 6,740,039 | B1 | 5/2004 | Rafter et al. | |
| 7,686,763 | B2 * | 3/2010 | Vaezy et al. | 600/439 |
| 7,713,209 | B2 * | 5/2010 | Guracar | 600/458 |
| 2005/0187476 | A1 | 8/2005 | Chomas et al. | |
| 2006/0064018 | A1 | 3/2006 | Chomas et al. | |
| 2007/0016039 | A1 * | 1/2007 | Vortman et al. | 600/439 |

FOREIGN PATENT DOCUMENTS

WO WO 2008/150326 12/2008

OTHER PUBLICATIONS

U.S. Appl. No. 11/713,209, filed on Mar. 2, 2007.
U.S. Appl. No. 11/805,151, filed on May 21, 2007.
Katherine W. Ferrara; "Contrast-enhanced quantitative ultrasound imaging of cancer: Developing a system and signal processing"; UCDavis Biomedical Engineering; http://ferraralab.bme.ucdavis.edu/nav_frame.html, Nov. 9, 2007.
PCT Search Report and Written Opinion for EP 08171688 application (counterpart of the above-identified US application), Apr. 2, 2009, 7 pages.

* cited by examiner

*Primary Examiner* — Long V Le
*Assistant Examiner* — Colin T Sakamoto

(57) ABSTRACT

The effectiveness of contrast agent destruction is determined. Locations of ineffectively destroyed contrast agents are identified. The response from undestroyed contrast agents may be distinguished from response from tissue due to saturation or from rapid perfusion. The locations may be highlighted on resulting images, indicating to the user locations not associated with perfusion. The user may make a diagnosis on perfusion rather than a lack of destruction of contrast agents.

9 Claims, 2 Drawing Sheets

CONTRAST AGENT DESTRUCTION EFFECTIVENESS DETERMINATION FOR MEDICAL DIAGNOSTIC ULTRASOUND IMAGING

BACKGROUND

The present embodiments relate to medical diagnostic ultrasound imaging of contrast agents. In particular, destruction and imaging subsequent perfusion of contrast agents is provided.

Various techniques may be used to image contrast agents with ultrasound energy. The reperfusion of contrast agents within the body is monitored after a sequence of higher power destruction frames. The rate at which tissue is reperfused may indicate the level of vascularity. Vascularity may indicate the health of the tissue or the effectiveness of a chemotherapeutic or ablative treatment of a cancerous region. If the tissue is not completely cleared of contrast agents prior to monitoring perfusion, the rate measurements may not be accurate, and possible misdiagnosis may occur.

One technique for monitoring perfusion is a maximum intensity projection image. The maximum intensity for each spatial location over a period is displayed. The maximum intensity projection of the contrast agent perfusion indicates the structure and extent of blood flow within a region. Insufficiently cleared contrast agent prior to maximum intensity projection may degrade the spatial resolution of this display of the vascular architecture.

BRIEF SUMMARY

By way of introduction, the preferred embodiments described below include methods, systems, computer readable media, and instructions for determining effectiveness of contrast agent destruction. The locations of ineffectively destroyed contrast agents are identified. The response from undestroyed contrast agents may be distinguished from response from tissue due to saturation or from rapid perfusion. The locations may be highlighted on resulting images, indicating to the user locations not associated with perfusion.

In a first aspect, a method is provided for indicating effectiveness of contrast agent destruction. Acoustic energy destroys contrast agents within a region. Locations within the region of incomplete destruction of the contrast agents are detected. The locations within the region are indicated.

In a second aspect, a computer readable storage medium has stored therein data representing instructions executable by a programmed processor for determining effectiveness of contrast agent destruction. The storage medium includes instructions for acquiring a baseline frame of data of contrast agent response after transmission of destruction pulses, and distinguishing, as a function of the baseline frame of data, between thermal noise, non-linear response of tissue signals, or both and contrast agent response associated with the incomplete destruction of contrast agents.

In a third aspect, a system is provided for determining effectiveness of contrast agent destruction. A transmit beamformer is operable to transmit first pulses for destruction of contrast agents and operable to transmit second pulses for imaging contrast agents with minimal destruction. A receive beamformer is operable to form contrast agent signals responsive to the second pulses. The timing for the first and second pulses is operable to distinguish between contrast agent response associated with rapid perfusion and contrast agent response associated with incomplete destruction.

The present invention is defined by the following claims, and nothing in this section should be taken as a limitation on those claims. Further aspects and advantages of the invention are discussed below in conjunction with the preferred embodiments.

BRIEF DESCRIPTION OF THE DRAWINGS

The components and the figures are not necessarily to scale, emphasis instead being placed upon illustrating the principles of the invention. Moreover, in the figures, like reference numerals designate corresponding parts throughout the different views.

DETAILED DESCRIPTION OF THE DRAWINGS AND PRESENTLY PREFERRED EMBODIMENTS

Users may desire to know that perfusion imaging starts from a volume completely cleared of contrast agents or to know where undestroyed contrast agents are located. For example, a maximum intensity projection image is captured or generated. Those portions of the image that are regions with insufficient destruction energy are indicated. The user may perform the imaging again and increase the amount of destruction or lower the concentration of the agent. Alternatively, the user may discount the portions in diagnosis. The user may determine if a new injection is necessary or if additional destruction energy is needed based on the area and shape of the indicated destruction effectiveness image. In one embodiment of indication, the user sees vessels and regions with very high levels of perfusion in a contrasting color.

In the final captured image, a unique color or highlighting may be provided for regions with contrast agents that were not cleared by the destruction energy. This highlighting may distinguish from one or more of the other sources. Different sources may contribute information similar to contrast agents. Saturation from bright targets, such as tissue, and thermal noise may be detected as contrast agents. Larger blood vessels or highly perfused regions where agent flows into the volume of interest very quickly may provide contrast agent response immediately after destruction and be misinterpreted as undestroyed contrast agent.

Figure 1:
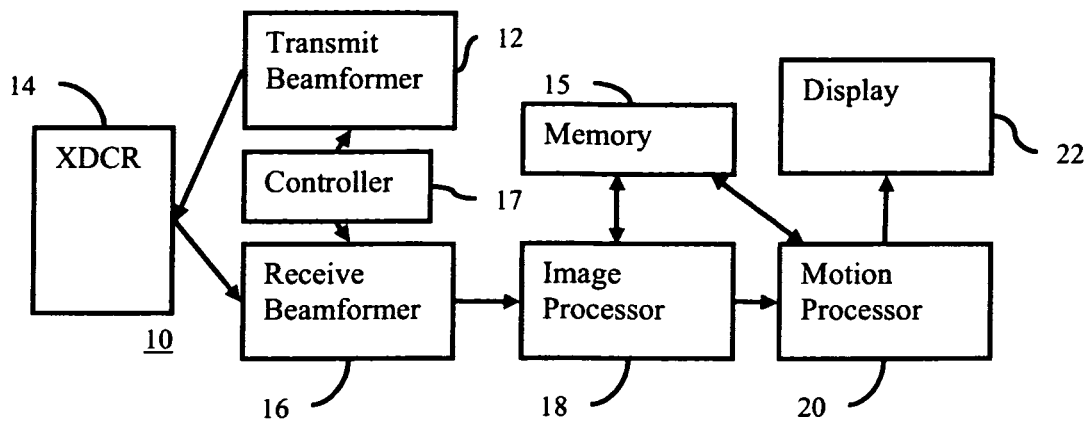
FIG. 1 is a block diagram of one embodiment of an ultrasound imaging system for determining effectiveness of contrast agent destruction.

FIG. 1 shows a system 10 for determining effectiveness of contrast agent destruction in medical diagnostic ultrasound imaging. The system 10 includes a transmit beamformer 12, a transducer 14, a memory 15, a receive beamformer 16, a controller 17, an image processor 18, a motion processor 20, and a display 22. Additional, different, or fewer components may be provided. For example, the motion processor 20 is combined with or part of the image processor 18. As another example, the controller 17 is part of the receive beamformer 16, the transmit beamformer 12, both, or another component.

The system 10 is a medical diagnostic ultrasound imaging system in one embodiment, but other imaging systems of the same (ultrasound) or different modality may be used. In other embodiments, part or all of the system 10 is implemented in a computer or workstation. For example, previously acquired frames of data are processed without the beamformers 12, 16 or transducer 14.

The transmit beamformer 12 is an ultrasound transmitter, memory, pulser, analog circuit, digital circuit, or combinations thereof. The transmit beamformer 12 is operable to generate waveforms for a plurality of channels with different or relative amplitudes, delays, and/or phasing. Upon transmission of acoustic waves from the transducer 14 in response to the generated waves, one or more beams are formed. The transmit beamformer 12 may cause the beam to have a particular phase and/or amplitude. For example, the transmit beamformer 12 transmits a sequence of pulses associated with a given scan line or to adjacent scan lines. The pulses correspond to beams with different amplitudes and/or relative phases. In alternative embodiments, a single beam is used for any given scan line and/or beams with a same amplitude and/or relative phases are used.

For contrast agent destruction, waveforms of acoustic energy have a mechanical index of about 1.0 MI or higher. The acoustic energy causes at least some contrast agents to burst or be absorbed. The frequency, amplitude, power, focus, or other characteristic of the waveforms or acoustic beam may be set to provide the desired destruction. Focal region, beam width, pulse repetition frequency, scan pattern, or other characteristic may be altered to destroy contrast agents more efficiently. In one embodiment, the transmit beamformer 12 includes the components, operation, and/or programming disclosed in U.S. Pat. No. 6,340,348, the disclosure of which is incorporated herein by reference, for transmitting destruction energy.

For imaging contrast agents, acoustic energy with a lower mechanical index (MI) is generated. For example, acoustic energy of 0.7 MI or lower is used to limit or avoid destruction of contrast agents. Acoustic energy with higher MI, such as associated with destruction of contrast agents may also be used for imaging.

The transducer 14 is a 1-, 1.25-, 1.5-, 1.75- or 2-dimensional array of elements. The transducer 14 includes a plurality of elements for transducing between acoustic and electrical energies. The elements are piezoelectric or capacitive membrane based structures. The elements connect with channels of the transmit and receive beamformers 12, 16.

The receive beamformer 16 includes a plurality of channels with amplifiers, delays, and/or phase rotators, and one or more summers. Each channel connects with one or more transducer elements. The receive beamformer 16 applies relative delays, phases, and/or apodization to form one or more receive beams in response to each transmission. The focused information from the channels is summed dynamically. In alternative embodiments, the receive beamformer 16 is a processor for generating samples using Fourier or other transforms.

The receive beamformer 16 may include a filter, such as a filter for isolating information at a second harmonic or other frequency band relative to the transmit frequency band. Such information may more likely include desired tissue, contrast agent, and/or flow information. In another embodiment, the receive beamformer 16 includes a memory or buffer and a filter or adder. Two or more receive beams are combined to isolate information at a desired frequency band, such as a second harmonic, cubic fundamental, or other band.

The receive beamformer 16 forms contrast agent signals responsive to the ultrasound pulses transmitted for imaging. Any desired sequence of transmit and receive operation may be used to obtain ultrasound information. For example, B-mode data may be obtained by scanning a region once and detecting the intensity of any response. The B-mode may be used for tissue imaging. Correlation or motion tracking may be used to derive fluid information from B-mode data. B-mode operation may provide contrast agent information, such as by filtering to isolate information at a second harmonic. Doppler information may be obtained by transmitting sequences of beams along each scan line. A corner turning memory may be used to isolate tissue, contrast agents, and/or flow information from Doppler signals. Other now known or later developed modes may be used.

In one embodiment, the mode is a contrast agent-imaging mode. Contrast agents may be imaged with typical B-mode or Doppler techniques. Contrast agent information is information primarily responsive to contrast agents, and tissue information is information primarily responsive to tissue. Isolating information at the second, even, odd, sub, or other harmonics may more likely identify information from contrast agents. For example, a two-pulse technique is used. The pulses have a same amplitude, but different phase. By summing the response, information associated with even harmonics is identified. Filtering may alternatively be used. Alternatively or additionally, relative phasing is provided in the receive processing.

In one embodiment, the transmit sequence is controlled to generate echo signals responsive to the cubic fundamental. The beamformer 12 is operable to transmit a plurality of pulses having at least two different amplitude levels and at least two of the plurality of pulses having opposite or different phases. Transmitter power can be varied in any suitable manner, as for example by adjusting the voltage applied to individual transducer elements, or by adjusting the number of transducer elements (or transmit aperture) used to form a particular pulse.

For obtaining ultrasound data at the cubic fundamental, the receive beamformer 16 includes line memories and a summer or a filter to combine signals responsive to the transmissions. The line memories or buffers can be formed as physically separate memories or can be formed as selected locations in a common physical device. The beamformed signals are stored in the line memories or buffers and then weighted and summed in a weighted summer. The memories and the summer can be implemented using analog or digital techniques. The weighted summer forms a composite output signal by weighting the separate beamformed receive signals. The composite output signal for a given spatial location is a sample associated with the cubic fundamental response.

Obtaining cubic fundamental information is disclosed in U.S. Pat. No. 6,494,841, the disclosure of which is incorporated herein by reference. Any of the transmit sequences and receive combinations disclosed therein may be used for obtaining cubic fundamental information. Other transmit sequences and receive combinations for obtaining cubic fundamental information may be used, such as disclosed in U.S. Pat. Nos. 6,602,195, 6,632,177, 6,638,228 and 6,682,482, the disclosures of which are incorporated herein by reference. In general, a sequence of pulses with different amplitudes and phases are transmitted. Using amplitude change or different amplitudes without different phases may also be used to obtain cubic fundamental information. By combining received signals responsive to the sequence, a sample including cubic fundamental information is obtained. The cubic fundamental information is highly specific to ultrasound contrast agents since contrast agents produce cubic response and the transducer and tissue produce very little cubic response. The information provides tissue clutter rejection, allowing for imaging more specific to contrast agents. For example, small vessels within tissue may be more easily imaged or identified using cubic fundamental information.

The controller 17 is a processor, application specific integrated circuit, digital signal processor, field programmable gate array, digital circuit, analog circuit, or combinations thereof. The controller 17 controls operation of the transmit and receive beamformers 12, 16. For example, the controller 17 causes the transmit beamformer 12 to transmit destruction pulses. As another example, the controller 17 causes the transmit beamformer 12 to transmit pulses and the receive beamformer 16 to receive responsive signals for imaging contrast agents. The controller 17 may control the timing of the transmission of pulses and/or reception.

The image processor 18 is a B-mode detector, Doppler detector, pulsed wave Doppler detector, correlation processor, Fourier transform processor, application specific integrated circuit, general processor, control processor, field programmable gate array, digital signal processor, analog circuit, digital circuit, combinations thereof or other now known or later developed device for detecting information for display from beamformed ultrasound samples. In one embodiment, the image processor 18 implements a fast Fourier transform from a plurality of samples representing a same region or gate location. Each of the samples is responsive to the cubic fundamental so that a pulsed wave Doppler display may be generated from cubic fundamental information. The image processor 18 also includes a B-mode detector in a parallel track. The B-mode detector operates on the same or different beamformed samples to detect tissue, contrast agent, or tissue and contrast agent response. For example, one receive beam for each spatial location from the sequence of receive beams used for cubic fundamental isolation is applied to the B-mode detector for imaging primarily tissue information.

The image processor 18 outputs frames of ultrasound data. The frames of data are formatted in an acquisition format (e.g., polar coordinate), a display format (e.g., scan converted into a Cartesian coordinate format or an image), or other format. Each frame of data represents a one, two, or three-dimensional scanned region. The frames of data include a single or multiple types of data. For example, one frame of data includes just contrast agent information. As another example, one frame of data includes contrast agent information for some spatial locations and another type of information (e.g., B-mode or Doppler) for other spatial locations. Different types of data may be provided in the same frame for a same spatial location. In another example, the different types of data are provided in different frames of data.

In an alternative embodiment, the image processor 18 loads data from a network or memory 15. For example, DICOM or other images are loaded. Each image is a frame of data. One frame may include different types of data, one overlaid on another. Alternatively, each frame includes only one type of data with different frames for different data types. In another embodiment, each frame is subdivided so that one portion includes one type of data and another portion includes another type of data with or without overlap of the represented spatial locations.

The image processor 18 may form a baseline frame of data. The baseline frame of data is formed from contrast agent information, such as from a cubic fundamental response. Other data sources may be included or alternatively used. The baseline frame of data is formed from information acquired after transmission of destruction pulses. For example, one or more scans of destruction pulses are transmitted. After allowing reverberations to die down, a frame of contrast agent data is acquired. As another example, line interleaving is used. Destruction pulses for one or more lines are transmitted, and the contrast agent information is acquired for the one or more scan lines. The process then repeats for different scan lines to complete the scan of the region. Other baseline frames of data may be used, such as a baseline stored from a previous imaging session or a modeled baseline.

The image processor 18 may form subsequent frames of data. For example, contrast agent response is detected for a plurality of scans without further interleaved destruction pulses. The subsequent frames with or without the baseline frame are used for imaging, such as forming a sequence of images or generating a frame of data representing a maximum intensity over a period for each location of a scan region.

The image processor 18 identifies locations associated with undestroyed contrast agents. For example, the baseline frame of data indicates locations. Any value above a threshold is considered undestroyed contrast agent. To isolate further undestroyed contrast agent from other response in the baseline frame of data, the image processor 18 may distinguish contrast agent response for incomplete destruction from tissue leakage, saturation, thermal noise, and/or rapid perfusion.

As an alternative to the image processor 18, the motion processor 20 may detect incomplete destruction of contrast agents. The motion processor 20 is an application specific integrated circuit, correlation processor, Fourier transform processor, general processor, control processor, field programmable gate array, digital signal processor, analog circuit, digital circuit, buffer, memory, combinations thereof, or other now known or later developed device for determining relative motion between frames of data and of detected contrast agent. The motion processor 20 stabilizes motion between frames of ultrasound data. For example, B-mode or tissue information is used to track motion between frames, and the same information and contrast agent information are aligned from frame-to-frame based on the tracked motion.

The motion processor 20 generates an image for the display 22. The image is generated from one or more frames of ultrasound data. For example, contrast agent information for a single frame or sequence of frames is color coded as a function of the locations of incomplete destruction. Where a spatial location for a given frame indicates incomplete destruction of contrast agent, the detected contrast agents are colored or otherwise highlighted differently than other contrast agents.

Another example display is a combination of data from a plurality of frames of data after spatial alignment. The motion processor 20 may include a persistence filter, other filter, summer, alpha blending buffer, other buffer, memory, processor, adder, or other device for generating an image from information of different frames of data. For example, the motion processor 20 compares data for a particular spatial location from one frame to another frame or an ongoing combination frame. Based on the comparison (e.g., highest value, contribution to mean value, or lowest value), one of the values is selected or the ongoing combination frame is updated to include the desired value (e.g., maximum intensity projection). As another example, the motion processor 20 determines an average, total, or other value representing a location or region as a function of time.

The display 20 is a CRT, monitor, LCD, flat panel, projector or other display device. The display 20 receives display values for displaying an image. The display values are formatted as a one-dimensional image, two-dimensional image, or three-dimensional representation. In one embodiment, the display values are for an image generated as a function of frames of data acquired at different times, such as a time intensity curve (TIC) or maximum intensity projection (MIP) image. As additional frames of data are acquired and selected, the image may be updated. Other images, such as images from single or component frames of data, may also be displayed.

In the image or images, one or more spatial locations (e.g., pixels) are modulated as a function of the determination of incompletely destroyed contrast agents. For example, such pixels are uniquely colored or modulated with color. Other information may be modulated or displayed with the incompletely destroyed contrast agents, such as rapid perfusion and/or tissue response. In one embodiment, locations associated with rapid perfusion and/or tissue response are not modulated in a same way as the incompletely destroyed contrast agents.

The memory 15 is a buffer, random access memory, read only memory, cache, hard drive, removable, optical, flash, system memory, combinations thereof, or other now known or later developed device for frames of data, images and/or instructions. The memory 15 may be a combination of different memory devices or separately addressed regions. In one embodiment, the memory 15 stores data to be used, during use, or after processing for the processors 18 and/or 20.

The image processor 18 and/or motion processor 20 operate pursuant to instructions. A computer readable storage medium stores data representing instructions executable by one or both of these programmed processors for determining effectiveness of contrast agent destruction in medical diagnostic ultrasound imaging. The instructions for implementing the processes, methods and/or techniques discussed herein are provided on computer-readable storage media or memories 15, such as a cache, buffer, RAM, removable media, hard drive or other computer readable storage media. Computer readable storage media include various types of volatile and nonvolatile storage media. The functions, acts or tasks illustrated in the figures or described herein are executed in response to one or more sets of instructions stored in or on computer readable storage media. The functions, acts or tasks are independent of the particular type of instructions set, storage media, processor or processing strategy and may be performed by software, hardware, integrated circuits, firmware, micro code and the like, operating alone or in combination. Likewise, processing strategies may include multi-processing, multitasking, parallel processing and the like. In one embodiment, the instructions are stored on a removable media device for reading by local or remote systems. In other embodiments, the instructions are stored in a remote location for transfer through a computer network or over telephone lines. In yet other embodiments, the instructions are stored within a given computer, CPU, GPU or system.

Figure 2:
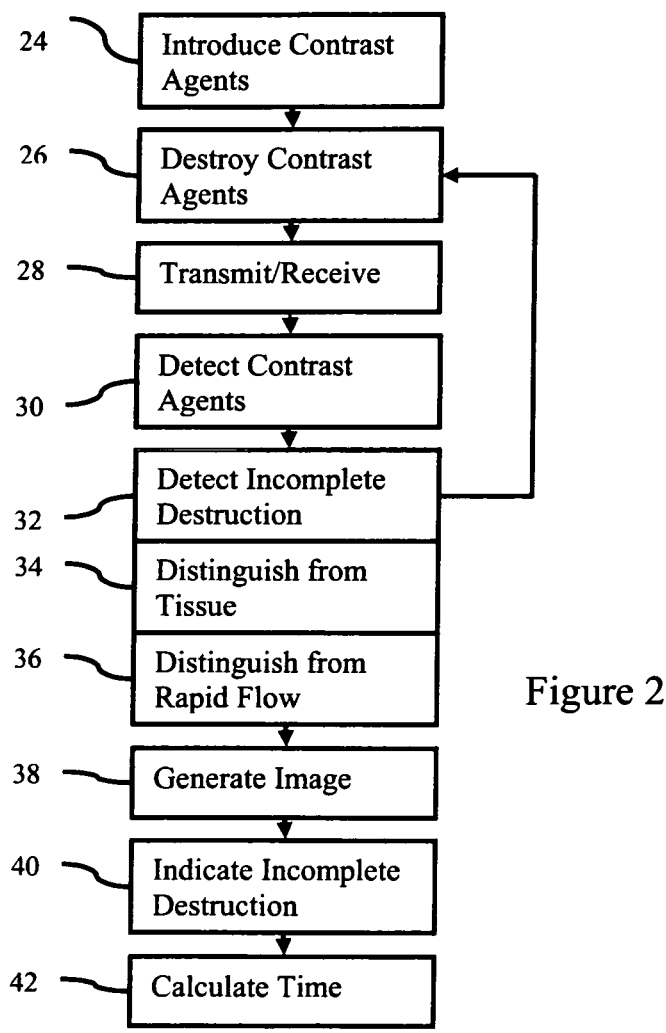
FIG. 2 is a flow chart diagram of a method for determining effectiveness of contrast agent destruction according to one embodiment.

FIG. 2 shows a method for indicating or determining effectiveness of contrast agent destruction in medical diagnostic ultrasound imaging. The method is implemented by the system 10 of FIG. 1 or a different system. The method is performed in the order shown or a different order. Additional, different, or fewer acts may be provided. For example, acts 26, 28, and 32 are provided with none or only some of the other acts. As another example, act 32 is performed without acts 34 and/or 26. In another example, acts 38, 40, 42, or the feedback from act 32 to act 26 are optional or are provided in any combination or subset. The acts are performed for a volume or two-dimensional region, such as frames of data representing the volume or two-dimensional region.

In act 24, contrast agents are introduced into a patient. The contrast agents are injected as a bolus manually or with a pump through a catheter or syringe. The contrast agents are injected into the bloodstream or other conduction path. The contrast agents may be of any number. In one embodiment, a limited number of contrast agents are injected to reduce the number of free flowing contrast agents. In another embodiment, a large number of contrast agents are injected.

The contrast agents are microbubbles with or without a shell. The contrast agents may include or be formed from therapeutic material, such as drugs for the treatment of a patient. The surface of the contrast agents may bind to or stick to tissue. In one embodiment, the contrast agents include ligands or other material or structure to more likely bind or stick to tissue. The material or structure may be targeted to bind or stick to specific tissues, such as deceased or inflamed tissue. In other embodiments, the contrast agents are provided for enhanced ultrasound imaging without other therapeutic structure.

Before or after any imaging, contrast agents are destroyed in act 26. For example, the user views contrast agents and/or tissue during an initial perfusion or inflow of contrast agents. Once the presence of contrast agents and the desired imaging region are confirmed, the contrast agents may be destroyed to calibrate or establish a desired initial condition (e.g., baseline). After destruction, the contrast agents re-perfuse the region of interest. In alternative embodiments, substantial numbers of contrast agents are not destroyed.

For destruction, acoustic energy sufficient to destroy some or all of the contrast agents is transmitted. For example, acoustic energy with a mechanical index 0.7 or higher at one or more locations is transmitted. To assure more likely destruction, a plurality of acoustic beams with a higher power (e.g., MI of 1.0 or higher) is transmitted along each of a plurality of scan lines. Different or the same focus or other beam characteristics may be used for each beam formed along a scan line. Since acoustic echoes are substantially not received in response to the destruction transmitting, more power may be provided by a short pulse repetition interval. Multiple transmit beams may be used to substantially destroy contrast agents in a given region, such as a scan region for sector, Vector®, or linear imaging. The region may be a region of interest or an entire field of view.

The destruction occurs automatically. A trigger event, such as time or change in intensity, activates the destruction. Alternatively, the destruction is activated manually. For example, the user depresses a button to trigger transmission of color Doppler pulses at a high power without reception.

In act 28, transmission and reception occurs for generating a sequence of ultrasound frames of data representing contrast agents. Acoustic beams with a lower power are transmitted along the scan lines of a region, and echoes responsive to the acoustic beams are received. The lower power is provided by a mechanical index of 0.7 or lower, lower frequency waveforms, smaller aperture, slower pulse repetition frequency, combinations thereof, or other beam characteristic.

In act 30, contrast agents are detected. The region scanned in act 28 includes contrast agents or an area that may include contrast agents. The contrast agents respond to ultrasound energies. Immediately after transmission of the destruction pulses, some or the entire region is free of contrast agents. However, one or more locations may have contrast agents due to incomplete destruction and/or rapid in-flow. A first imaging frame of data after destruction may include information from contrast agents. The information may also include response from tissue or fluids. In one embodiment, the information is obtained at a cubic fundamental of ultrasound signals. For example, ultrasound signals are transmitted in a plurality of pulses having at least two different amplitude levels and phases. Signals responsive to the transmissions are combined. Data is acquired at each spatial location of a region of interest in each frame of data.

The intensity, variation, velocity, power, or other characteristic of the response of the contrast agents is determined. In one embodiment, a B-mode detector is used for both contrast agent and tissue information detection. Alternatively, a separate detector, such as Doppler or other detector, is used to detect contrast agent information. The contrast agent information is detected using any technique with specificity to contrast agents. The same receive beamformed information or separate information is also used for determining the spatially registered B-mode or tissue information.

Only one type of data is represented in the frames of data, such as data representing just contrast agents or responses from contrast agent and tissue. Alternatively, the frames of data represent different types of data, such as in a same frame or in different sets of frames.

A sequence of frames of data is generated by acquiring frames of data with ultrasound, or by acquiring previously generated ultrasound frames of data (e.g., DICOM images). The frames of data are acquired in real time with live scanning or are from stored clips of detected data. The sequence may be substantially continuous or periodic (e.g., acquired once or more every heart cycle).

The sequence includes frames of data representing a scanned region at different times. Each frame of data represents a same or overlapping region. Some frames may represent different regions, such as due to out-of-plane motion of the transducer relative to the patient.

In act 32, one or more frames of data in the sequence are used to detect locations within the region of incomplete destruction of the contrast agents. For example, the first frame of data after destruction is used. Any response that may be from contrast agents is identified as incomplete destruction. The location of the response is determined.

In one embodiment, a baseline perfusion frame of data is acquired after the destroying. The baseline frame of data is the first frame of data acquired after destruction, such as acquiring as soon as possible after destruction while minimizing reflections from the destruction transmission. The baseline frame of data may include detected contrast agent response. For example, the first acquired cubic fundamental or other contrast agent imaging response obtained after the destruction pulses is a baseline perfusion image, $C_{baseline}$.

The locations of contrast agent response in the baseline frame of data are associated with incomplete destruction. Alternatively, the locations with contrast agent response exceeding a noise level by a threshold are associated with incomplete destruction. If detected signals within this frame exceed a signal-to-noise ratio threshold, then the signals are considered to be from undestroyed agent. The noise level may be measured by receiving in response to no transmission, estimated from the gain settings, or empirically determined.

Responses from tissue, thermal noise, saturation, or other sources that may appear as contrast agent response may be distinguished to further isolate response from incomplete destruction of contrast agents. In act 34, a distinction is made between thermal noise, saturation of tissue signals (e.g., non-linear response of tissue signals due to front-end saturation), or both and contrast agent response associated with the incomplete destruction. Tissue response may cause front-end saturation, leading to false contrast agent signals. Saturation is more likely to occur for reflections from tissue closer to the transducer. In the baseline frame of data, the regions in the near field more likely show saturation and tissue signal leakage than other regions. Since the destruction energy is more widely distributed or less focused in the near field, the near field may more likely include undestroyed agent than other regions.

To distinguish, locations associated with tissue are identified. For example, signal from tissue is associated with a large B-mode signal intensity. Using a separate scan or at least some of the beamformed samples from the contrast agent detection, B-mode detection is performed. In one embodiment, the frame of B-mode data is acquired immediately after completion of the destruction. The B-mode frame of data may be acquired at another time, such as before performing act 24. Locations associated with B-mode data exceeding a threshold are excluded from the undestroyed agent indication. These locations may be blacked out, replaced, or uniquely highlighted in subsequent imaging to show or not show tissue leakage or saturation.

For undestroyed contrast agents, locations not associated with tissue are used. For example, the locations associated with the B-mode tissue response being less than a threshold level and not being associated with the B-mode tissue response exceeding the threshold are identified. For undestroyed contrast agents, the baseline frame of data is used to identify locations with a signal-to-noise ratio exceeding a first threshold. A subset of these locations corresponds to a B-mode intensity below a second threshold. The subset of locations is identified as undestroyed contrast agents.

Regions associated with a vessel may have rapid in-flow of contrast agents. Since reverberations from the destruction pulses are allowed to die down before obtaining the baseline frame of data, some contrast agents may flow into regions where contrast agent was destroyed. The flow may result in contrast agents being detected in the baseline frame of data. If this artifact is acceptable, these contrast agents are indicated as due to incomplete destruction.

Alternatively, detection of contrast agents associated with rapid inflow may be avoided. In act 36, contrast agent response associated with rapid perfusion is distinguished from contrast agent response associated with the incomplete destruction. Location within the scan region, size and shape of regions of detected contrast agent, or other characteristic may be used.

Alternatively or additionally, rapid inflow may be distinguished from incomplete destruction by avoiding detection of the rapid in-flow contrast agents in the baseline frame of data. The timing for the destruction and imaging pulses or transmissions may distinguish between contrast agent response associated with rapid perfusion and contrast agent response associated with incomplete destruction.

One sequence of destruction pulses (D) and imaging pulses (C) interleaves by frame or scan. For example, four lines per frame of data are used. A greater number of scan lines may be provided. Each destruction pulse D represents a single pulse of high power. Each C represents a triplet of three pulses with the first and last pulse with ½ amplitude and the middle pulse with full amplitude and opposite phase for detection of cubic fundamental response. The sequence is represented as: $D_0 D_1 D_2 D_3 D_0 D_1 D_2 D_3 D_0 D_1 D_2 D_3 C_0 C_1 C_2 C_3 C_0 C_1 C_2 C_3 C_0 C_1 C_2 C_3 \ldots$. The first sequence C after detection provides the baseline perfusion frame. This baseline frame may be used to indicate regions of incomplete destruction, but may include contrast agent response from rapid inflow.

Using line interleaving of transmissions for the destroying with transmissions for detecting contrast agents may further distinguish rapid inflow from incomplete destruction. The timing of pulses is set to provide line interleaving of destruction and imaging pulses. Rather than complete scans of the scan region for each destruction and imaging sequence, multiple destruction pulses are transmitted along a scan line, followed by transmission of imaging pulses along the same scan line. After completing that scan line, the process is repeated for another scan line. Subsequent imaging occurs without destruction pulses. Destruction and/or imaging pulses along other scan lines may intervene.

In one example of line interleaving, a sequence of pulses with reduced time between destruction and detection of contrast agents is transmitted. The reduced time improves the differentiation between incomplete destruction and rapid perfusion. Using the D and C designation in the example above, one example sequence is: $D_0 D_1 D_2 D_3 D_0 D_0 C_0 D_1 D_1 C_1 D_2 D_2 C_2 D_3 D_4 C_3 C_0 C_1 C_2 C_3 C_0 C_1 C_2 C_3$ . . . . In this sequence, the baseline perfusion frame is acquired in a line-interleaved fashion with one or more high amplitude destruction pulses. Fewer contrast agents from rapid inflow are likely to be detected in the baseline frame of data.

To distinguish further rapid inflow from incomplete destruction, the first complete frame after all destruction events (in italic) is compared with the baseline perfusion frame to determine regions of rapid inflow. Rapid inflow occurs in the same location due to vessel structure. These regions are positively identified in the first complete frame of data. These regions are ruled out for incomplete destruction from the baseline frame of data. The remaining locations of contrast agent in the baseline frame of data are considered to be from incomplete destruction.

In act 38, an image representing perfusion of the region is generated. For example, the baseline frame of data and subsequent frames of data are used to generate a sequence for frames of data showing perfusion. As another example, the frames of data are combined to generate one or more images. One combination is low pass filtering the frames of data. Another example combination is forming a motion compensated maximum intensity projection image of contrast agent response after the destroying. Frames subsequent to or including the baseline perfusion frame are accumulated using a motion compensated maximum intensity projection (MIP) over a period, such as accumulating frames of data from 1 to 20 seconds. Any period may be used with the baseline frame acquired at one second or other time. A sequence of images associated with accumulating different periods (e.g., baseline to 5 second, baseline to 10 seconds . . . ) may be generated.

Since frames are acquired over time, motion compensation may be used to limit or avoid blurring due to transducer and/or patient motion. Motion between frames of ultrasound data is corrected. The spatial relationship between a reference frame (e.g., the baseline frame) and other frames or between sequentially adjacent frames is stabilized. For each new frame of data, the previous or temporally adjacent selected frame of data is used as the reference frame. Alternatively, the same reference frame is used for comparison to each temporally spaced frame of data.

The spatial relationship of the contrast agent information is corrected. The motion may be determined using the contrast agent information. In other embodiments, B-mode or tissue information is used for correcting motion for the contrast agent information. Stabilization is performed in the acoustic domain, the Cartesian domain or any other coordinate space.

The motion is tracked. Data from one frame of data is correlated with different regions in the other frame of data to identify a best or sufficient match. A correlation, cross-correlation, minimum sum of absolute differences, or other function indicates a level of similarity between two frames of data. By repositioning one frame of data relative to another frame of data in a search pattern, the level of match or similarity is determined for various relative positions. Any search pattern may be used, such as searching based on previous motion, course and fine search sequences, or searching based on typical motion. The position associated with the greatest similarity indicates the motion between the frames of data.

Global or local motion may be corrected. For global motion, the entire frames of data are used. Alternatively, regions of interest, such as a region about ⅓ of the total area or volume is used for comparison. The region searched may be limited, such as only searching within a particular range. For local motion, a plurality of regions may be separately tracked. A final motion is determined as a function of the motion for each sub-region, such as by averaging.

Motion is corrected by determining a relative translation and/or rotation along one or more dimensions. The motion is determined in one or more dimensions. The motion may be only lateral, in plane for two-dimensional imaging, or along three axes for three-dimensional scanning. Optionally, an amount of rotation around or more axes may be determined.

After determining relative motion, alignment reassigns spatial locations. The spatial locations of each frame of data are reassigned based on the motion relative to the reference. The reassignment spatially aligns the ultrasound frames of data as a function of the tracking. Rigid or non-rigid correction may be used. The motion correction may remove or lessen motion associated with transducer movement, patient movement, or organ movement. As an alternative, alignment is not performed. Any spatial offset due to the motion is calculated as needed from the motion.

After correcting for motion, the MIP image is generated. For maximum intensity projection, the maximum value throughout the sequence is selected. For each spatial location in a region of interest, the maximum value from the spatially aligned ultrasound frames of data is determined and used for the image. In one embodiment, only a subset of the ultrasound frames of data from the sequence are used in the combination. For example, the frames of data are selected as a function of motion. Frames associated with a threshold amount of relative motion are not used in the combination. Frames of data when the transducer is in the proper field of view during the integration period (i.e. 20 seconds) are selected and used.

Motion correction between each frame may reduce blurring. However, certain forms of motion, such as out-of-plane motion, may not be corrected. Some blurring may still exist. To further reduce blurring or image artifacts in the combination over time, frame selection is performed based on the data acquired. Frames associated with substantial motion are not used in the combination, resulting in less blurring. Frame selection determines whether to integrate the information of a next frame for processing. The frames are selected based on similarity between frames, motion displacement parameters, or other characteristics.

U.S. Published Application No. 2008-0214934, the disclosure of which is incorporated herein by reference, describes embodiments of maximum intensity projection and selection of frames to be included in the maximum intensity projection image. The same selection or different selection criteria may be used for an integration, maximum intensity projection, or other combination. The non-selected ultrasound frames of data are not used for determining the display value or image. Other embodiments of maximum intensity projection, motion correction, and/or selection of frames of data are disclosed in U.S. Published Application No. 2008-0294049, the disclosure of which is incorporated herein by reference.

After selection, the frames of data are used for maximum intensity projection. The resulting image represents the maximum value of contrast agent response for each spatial location through the sequence. The MIP image may be combined with a reference frame of B-mode information or displayed alone.

The locations associated with incomplete destruction are indicated in act 40. The locations are indicated in a separate image. Alternatively, the locations are highlighted in the MIP or other image. Display values for corresponding spatial locations are modulated or weighted by the binary determination of incomplete destruction. Alternatively, the locations are displayed in a color (e.g., red) different than other colors in an image responsive to the received echoes. A color or other map is selected based on the determination. For spatial locations with incomplete destruction of contrast agent, a different color or map is used than for other locations.

The highlighting may be performed prior to or after the combination. For example, the maximum intensity projection (MIP) for contrast agent responses is determined for each spatial location. Contrast agents are coded with darker colors. Locations of incomplete destruction of contrast agents are coded with bright colors. The coded information is combined. As another example, the contrast agent information is combined. The results are then coded.

Other information may be coded differently or relatively adjusted to highlight or not highlight. For example, the image has a relatively adjusted contribution of the thermal noise, non-linear response of tissue signals, or both and contrast agent response associated with the incomplete destruction of contrast agents. Color coding highlights different regions. For example, green indicates regions of saturation and tissue leakage. These locations have signal in the baseline perfusion region as well as large signal levels in the low pass filtered version of the underlying B-mode image. Blue indicates regions where the B-mode is not so large and where information is visible in the baseline perfusion region, representing incomplete destruction of contrast agents.

Some of the blue may be regions from areas of very rapid perfusion. The technique disclosed above to differentiate regions of rapid perfusion and incomplete destruction allows these regions to be colored or otherwise indicated differently. For example, color coding resulting from only showing undestroyed agent is used. The tissue leakage or saturation regions are blacked out or replaced with a noise level. The tissue leakage or saturation signal may instead be retained, but not colored (e.g., displayed as gray scale values). Response from rapid inflow is not detected or is identified. The signal from rapid inflow may be coded based on contrast agent response (perfusion coding), but not highlighted like undestroyed contrast agents. Alternatively, the response from rapid inflow is displayed with a different coding (e.g., different color).

Figure 3:
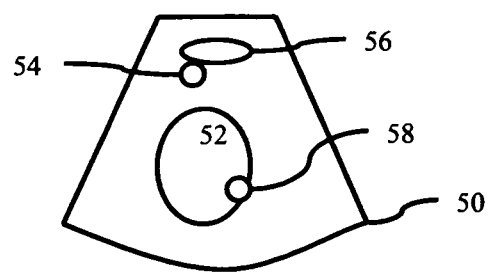
FIG. 3 is a graphical representation of a maximum intensity projection image with an indication of undestroyed contrast agent.

As contrast agents perfuse the region, locations associated with contrast agent are shown in the MIP image. Vascular regions, perfused contrast agents, tissue leakage, saturation, thermal noise, and undestroyed contrast agents may also be shown. FIG. 3 shows a MIP image 50. The region 52 represents locations of perfusion. The region 52 is to be diagnoses as cancerous or not. The speed of perfusion may indicate vascularity. Vascularity may assist a medical professional with diagnosis. The size of the region after a particular period, the shape of the region, or other characteristic may assist in diagnosis.

Undestroyed contrast agents may distract from diagnosis. The upper region 54 represents incomplete destruction. The oblong upper region 56 represents tissue leakage or saturation. The lower small region 58 represents a large vessel associated with rapid inflow. In one embodiment, the incomplete destruction locations include the regions 54, 56, and 58. These regions are color coded or otherwise highlighted. In another embodiment, the tissue leakage or saturation region 56, the rapid inflow region 58, or both are removed or coded differently.

In act 42, the time for a contrast agent response to reach a threshold level is calculated. After destruction of the contrast agents, contrast agents reperfuse to particular locations. The time for the reperfusion to occur from the destruction may assist diagnosis. The arrival time is computed based on the signal exceeding a certain threshold and the time elapsed since destruction.

The time-to-peak augments the contrast agent information. The time-to-peak associated with each spatial location is determined. Any function may be used. In one example of time-to-peak calculation, a further threshold is incorporated. $C_{MIP}(t)$ is the maximum intensity projection (maximum value from time 0 to time t) of contrast agent image C from time 0, immediately after destruction, to current time, t. $C_{BaselinePerfusion}$ is the contrast agent image C at time 0, immediately after the destruction frames. $C_{BaselinePerfusion} = C_{MIP}(0) * C_{MaxPerfusion}$ is the contrast agent image C from time less than zero, immediately before the destruction frames. $C_{MaxPerfusion}$ represents the region fully perfused. The capture interval for the maximum intensity projection is selected by the user. If an indefinite interval is selected, the capture interval used in the time to peak calculation is replaced by a set value, such as 5 seconds.

One example time-to-peak algorithm applies a threshold and is:

$$\text{if } C_{MIP}(t) > timeToPeakThreshold$$
$$\text{then } T_{pk} = t \cdot \frac{255}{captureInterval}$$

If $C_{MIP}(t)$ is less than or equal to the threshold, then an event has not been reached during the interval t. The timeToPeakThreshld is 50, and the captureInterval is 5 in one example. The algorithm is for display in a range of 0-255.

Another example time-to-peak algorithm that corrects for maximum and baseline perfusion and is:

$$\text{if } C_{MIP}(T) - C_{BaselinePerfusion} - timeToPeakScaleFactor \cdot C_{MaxPerfusion} > timeToPeakThreshold$$
$$\text{then } T_{pk} = t \cdot \frac{255}{captureInterval}$$

If $C_{MIP}(t)$ is less than or equal to the threshold, then the event has not been reached in the interval t. With a timeToPeakScaleFactor=0.8, 80% of the maximum perfusion is used before the peak is declared. The timeToPeakThreshold may, in an example, be set to a small value, say 5 out of 255, to help reject noise.

The time-to-peak information includes values for each spatial location. The time-to-peak information may be filtered, such as spatially smoothing with a two dimensional boxcar filter. For example, a 6×6 boxcar filter is used. Other filters with a predetermined or adjustable number of taps may be used.

The maximum value or corresponding image value may be augmented with the time-to-peak information. For example, the brightness is increased for later arrivals—contrast agent with a later time-to-peak. One embodiment is represented by:

$$\tilde{C}_{MIP} = C_{MIP} + T_{pk}\frac{MaxMipAugmenationFromTpkdB}{bModeDynamicRange}$$

where bModeDynmicRange is the dynamic range of the B-mode information, and MaxMipAugmentationFromTpkdB is 10. As another example, the brightness of earlier arrivals is increased. On embodiment is represented by:

$$\tilde{C}_{MIP} = C_{MIP} + (255 - T_{pk})\frac{MaxMipAugmenationFromTpkdB}{bModeDynamicRange},$$

if $T_{pk} > 0$.

In other embodiments, the time information forms a separate image or is output as one or more values (e.g., a statistical value for locations associated with perfusion).

The locations associated with incomplete destruction are not included in the time calculations. Areas determined to be from undestroyed agent are tagged and excluded from the time-to-peak calculation. Undestroyed contrast agent may skew the time-to-peak statistics since almost immediate time-to-peak is provided.

A feedback loop is shown from act 32 to act 26. This optional feedback may allow the user or a processor to control destruction in act 26. For example, a baseline perfusion image is monitored. If there are significant regions of undestroyed agent, the destruction sequence is restarted with a greater number of destruction frames or increased transmitted power to clear, more effectively, the contrast agents. Where incomplete destruction occurs, additional destruction pulses may be transmitted. In response to detection of locations of incomplete destruction, the additional pulses are transmitted. The additional pulses are fired before or after performance of act 38, act 40, and/or act 42 during a perfusion study.

Additional destruction pulses may be transmitted in general, such as repeating one or more scans with destruction pulses. Alternatively or additionally, destruction pulses optimized to destroy contrast agents at the detected locations are transmitted. For example, the scan line, the focal depth, the aperture, or other pulse characteristic adapts to more likely destroy contrast agents at the locations of incomplete destruction. Greater energy is focused on only those areas that have large amounts of undestroyed agent.

While the invention has been described above by reference to various embodiments, it should be understood that many changes and modifications can be made without departing from the scope of the invention. It is therefore intended that the foregoing detailed description be regarded as illustrative rather than limiting, and that it be understood that it is the following claims, including all equivalents, that are intended to define the spirit and scope of this invention.

What is claimed:

1. A method for indicating effectiveness of contrast agent destruction, the method comprising:
   destroying, with acoustic energy, contrast agents within a region;
   forming a motion compensated maximum intensity projection image of contrast agent response after the destroying;
   detecting locations within the region of incomplete destruction of the contrast agents; and
   indicating the locations within the region differently from locations of perfusion of contrast agents in the motion compensated maximum intensity projection image.

2. The method of claim 1 wherein destroying comprises transmitting a first plurality of acoustic beams with a higher power along each of a plurality of scan lines, wherein acoustic echoes are substantially not received in response to the transmitting;
   further comprising transmitting second acoustic beams with a lower power along the scan lines and receiving echoes responsive to the acoustic beams,
   wherein indicating comprises highlighting the locations in a color different than other colors in an image responsive to the received echoes.

3. The method of claim 1 wherein detecting locations comprises distinguishing between contrast agent response associated with rapid perfusion and contrast agent response associated with the incomplete destruction.

4. The method of claim 3 wherein distinguishing comprises line interleaving of transmissions for the destroying with transmissions for detecting contrast agents.

5. The method of claim 1 wherein detecting locations comprises distinguishing between thermal noise, saturation of tissue signals, or both and contrast agent response associated with the incomplete destruction.

6. The method of claim 5 wherein distinguishing comprises identifying the locations as associated with the B-mode tissue response being less than a threshold level and not being associated with the B-mode tissue response exceeding the threshold.

7. The method of claim 1 wherein detecting comprises acquiring a baseline perfusion frame of data after the destroying, and identifying the locations from data of the frame of data exceeding a noise level by a threshold.

8. The method of claim 1 further comprising:
   controlling additional destruction pulses as a function of the locations, in response to detection of the locations, or both.

9. The method of claim 1 wherein further comprising calculating a time for a contrast agent response to reach a threshold from the destroying for the region without including the locations.

* * * * *